US010765416B2

(12) United States Patent
Li

(10) Patent No.: US 10,765,416 B2
(45) Date of Patent: Sep. 8, 2020

(54) LEFT ATRIAL APPENDAGE OCCLUDER

(71) Applicant: LIFETECH SCIENTIFIC (SHENZHEN) CO., LTD, Shenzhen (CN)

(72) Inventor: Anning Li, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 180 days.

(21) Appl. No.: 16/066,840

(22) PCT Filed: Jun. 20, 2016

(86) PCT No.: PCT/CN2016/086417
§ 371 (c)(1),
(2) Date: Jun. 28, 2018

(87) PCT Pub. No.: WO2017/113647
PCT Pub. Date: Jul. 6, 2017

(65) Prior Publication Data
US 2019/0021711 A1     Jan. 24, 2019

(30) Foreign Application Priority Data
Dec. 31, 2015  (CN) .......................... 2015 1 1033081

(51) Int. Cl.
*A61F 2/24* (2006.01)
*A61B 17/00* (2006.01)
(Continued)

(52) U.S. Cl.
CPC .......... *A61B 17/0057* (2013.01); *A61B 17/12* (2013.01); *A61B 17/12031* (2013.01);
(Continued)

(58) Field of Classification Search
CPC .......... A61B 17/0057; A61B 17/12122; A61B 17/12031
See application file for complete search history.

(56) References Cited

U.S. PATENT DOCUMENTS 6,152,144 A  * 11/2000 Lesh .................. A61B 17/0057
                                              128/898
7,972,359 B2 *  7/2011 Kreidler ............. A61B 17/0057
                                              606/213
(Continued)

FOREIGN PATENT DOCUMENTS

CN         1342056 A     3/2002
CN       103598902 A     2/2014
(Continued)

OTHER PUBLICATIONS

International Search Report dated Sep. 30, 2016 of corresponding International Application No. PCT/CN2016/086417; 8 pgs.
(Continued)

Primary Examiner — Wade Miles
Assistant Examiner — Mohammed S Adam
(74) Attorney, Agent, or Firm — Maier & Maier, PLLC

(57) ABSTRACT

A left atrial appendage occluder, including a closure disc and a bracket connected to the closure disc; the closure disc includes a frame; the frame includes a proximal-end disc face and a distal-end disc face; the proximal-end disc face includes flexible proximal-end support rods arranged radially; the distal-end disc face includes flexible distal-end support rods arranged radially; the floating end of each of the flexible proximal-end support rods is connected to the floating end of the adjacent flexible distal-end support rod The flexible proximal-end support rod at the point of largest diameter of the closure disc is arranged independent of the distal-end support rod; thus the degree of freedom of deformation at the point of largest diameter of the closure disc is
(Continued)

increased, ensuring that the outer edge of the closure disc may adapt to fit the openings of various irregular left atrial appendages.

19 Claims, 5 Drawing Sheets

(51) Int. Cl.
*A61B 17/12* (2006.01)
*A61F 2/04* (2013.01)

(52) U.S. Cl.
CPC .. *A61B 17/12122* (2013.01); *A61B 17/12145* (2013.01); *A61F 2/04* (2013.01); *A61B 2017/00592* (2013.01); *A61B 2017/00597* (2013.01); *A61B 2017/00632* (2013.01)

(56) References Cited

U.S. PATENT DOCUMENTS

| | | | | |
|---|---|---|---|---|
| 8,801,746 B1* | 8/2014 | Kreidler | ............... | A61F 2/01 606/200 |
| 9,808,201 B2* | 11/2017 | Braido | ............... | A61F 2/2418 |
| 2003/0220667 A1* | 11/2003 | van der Burg | ..... | A61B 17/0057 606/200 |
| 2004/0093017 A1* | 5/2004 | Chanduszko | ...... | A61B 17/0057 606/200 |
| 2005/0065589 A1* | 3/2005 | Schneider | .......... | A61B 17/0057 607/126 |
| 2005/0177182 A1* | 8/2005 | van der Burg | ..... | A61B 17/0057 606/157 |
| 2007/0118176 A1* | 5/2007 | Opolski | ........... | A61B 17/12122 606/213 |
| 2007/0162048 A1* | 7/2007 | Quinn | ............... | A61B 17/12122 606/113 |
| 2008/0249562 A1* | 10/2008 | Cahill | ................ | A61B 17/0057 606/215 |
| 2009/0099596 A1* | 4/2009 | McGuckin, Jr. | ... | A61B 17/0057 606/216 |
| 2012/0172927 A1* | 7/2012 | Campbell | .......... | A61B 17/0057 606/213 |
| 2012/0283585 A1* | 11/2012 | Werneth | ............. | A61B 17/0057 600/508 |
| 2013/0131717 A1* | 5/2013 | Glimsdale | ........ | A61B 17/12122 606/213 |
| 2013/0218192 A1* | 8/2013 | Erzberger | ........ | A61B 17/12122 606/200 |
| 2013/0218193 A1* | 8/2013 | Erzberger | ........ | A61B 17/12172 606/200 |
| 2013/0245666 A1* | 9/2013 | Larsen | ............. | A61B 17/12122 606/198 |
| 2014/0005714 A1* | 1/2014 | Quick | ................... | A61L 31/022 606/200 |
| 2014/0018841 A1* | 1/2014 | Peiffer | ............. | A61B 17/12122 606/200 |
| 2014/0074151 A1* | 3/2014 | Tischler | ........... | A61B 17/12122 606/200 |
| 2014/0135817 A1* | 5/2014 | Tischler | ............. | A61B 17/0057 606/200 |
| 2014/0364941 A1* | 12/2014 | Edmiston | ......... | A61B 17/12177 623/2.11 |
| 2015/0005810 A1* | 1/2015 | Center | ............. | A61B 17/12177 606/200 |
| 2015/0173770 A1* | 6/2015 | Warner | ............ | A61B 17/12172 606/200 |
| 2015/0196300 A1* | 7/2015 | Tischler | ........... | A61B 17/12172 606/191 |
| 2015/0342612 A1* | 12/2015 | Wu | .................. | A61B 17/12031 606/200 |
| 2017/0156898 A1* | 6/2017 | Obradovic | ....... | A61B 17/12122 |

FOREIGN PATENT DOCUMENTS

| | | |
|---|---|---|
| CN | 104352260 A | 2/2015 |
| CN | 104856741 A | 8/2015 |
| WO | 2007035497 A1 | 3/2007 |

OTHER PUBLICATIONS

Office Action dated Dec. 28, 2017 of corresponding Chinese Application No. 201511033081.6; 4 pgs.

* cited by examiner

LEFT ATRIAL APPENDAGE OCCLUDER

FIELD

The present disclosure relates to a medical device, and more particularly relates to a left atrial appendage occluder.

BACKGROUND

At present, an occluder may be put into a left atrial appendage through a catheter intervention method to prevent a thrombus from forming in the left atrial appendage due to atrial fibrillation and avoid apoplexy caused by the thrombus going up to a brain, or prevent systematic embolism caused by the thrombus reaching other portions of a body through the body's blood circulation system. Such left atrial appendage occluders substantially include an integrated occluder and a split type occluder according to their structures. For example, the split occluder generally includes a fixing frame and a sealing plate which are connected with each other; the fixing frame is disposed in a cavity of the left atrial appendage to fix the whole occluder; and the sealing plate seals an opening portion of the left atrial appendage to prevent blood flow from flowing into the cavity of the left atrial appendage.

For the split occluder of this type, its fixing frame and sealing plate have a connection restriction, wherein one component will be pulled by the other component, and the two components may not deform independently. For example, once the fixing frame is fixed in a cavity of the left atrial appendage, the fixing frame will pull the sealing plate when in a process of complying with a cavity structure of the left atrial appendage and its own movement of the left atrial appendage; and in the process, the sealing plate may not be fully fitted to an opening portion of the left atrial appendage and a blood flow channel will be formed between a left atrium and the left atrial appendage, so that an optimal sealing effect may not be achieved, and then the thrombus in the left atrial appendage flows out of the left atrial appendage, which will cause the apoplexy.

SUMMARY

In view of the above problems, it is necessary to provide a left atrial appendage occluder with better sealing effect and higher adaptability.

A technical scheme adopted to solve the technical problems is as follows: a left atrial appendage occluder is provided, including a sealing plate and a fixing frame connected with the sealing plate, the sealing plate includes a proximal disk surface and a distal disk surface; the proximal disk surface includes a number of elastic proximal supporting rods arranged in a radiated manner in a radial direction; the distal disk surface includes a number of elastic distal supporting rods arranged in a radiated manner in the radial direction; and a hanging end of each proximal supporting rod is connected with a hanging end of one distal supporting rod adjacent to the proximal supporting rod.

In one embodiment, the proximal disk surface includes a proximal seal head; one end of each proximal supporting rod is connected with the proximal seal head, and the other end of the proximal supporting rod is radiated in the radial direction and is hanging; the distal disk surface includes a distal seal head; and one end of each distal supporting rod is connected with the distal seal head, and the other end of the distal supporting rod is radiated in the radial direction and is hanging.

In one embodiment, the proximal seal head and the distal seal head are axially aligned; and a projection of each distal supporting rod in the proximal disk surface is basically overlapped with one proximal supporting rod connected with the distal supporting rod. In one embodiment, the proximal seal head and all of the proximal supporting rods are formed by integrated or integratedly cutting, and/or the distal seal head and all of the distal supporting rods are formed by integratedly cutting, and/or the proximal supporting rods and the distal supporting rods connected with the proximal supporting rods are formed by integratedly bending of one rod body.

In one embodiment, a proximal connection included angle between the proximal seal head and one proximal supporting rod is an acute angle, and a distal connection included angle between the distal seal head and one distal supporting rod is an acute angle.

In one embodiment, the proximal connection included angle between the proximal seal head and one proximal supporting rod is in a range from 15 degrees to 90 degrees or 60 degrees to 85 degrees, and the distal connection included angle between the distal seal head and one distal supporting rod is in a range from 15 degrees to 90 degrees or 60 degrees to 85 degrees.

In one embodiment, the distal supporting rod includes a distal connecting section and a distal hanging section; one end of each distal connecting section is connected with the distal seal head, and the other end of the distal connecting section is connected with one end of each distal hanging section; the other end of each distal hanging section is connected with the hanging end of one proximal supporting rod; and the distal hanging sections are basically perpendicular to the axial line of the distal seal head.

In one embodiment, the hardness of the distal connecting section is greater than that of the distal hanging section.

In one embodiment, the proximal supporting rod includes a proximal connecting section and a proximal hanging section; one end of each proximal connecting section is connected with the proximal seal head, and the other end of the proximal connecting section is connected with one end of each proximal hanging section; and the proximal hanging section of each proximal supporting rod is connected with one distal hanging section adjacent to the proximal hanging section.

In one embodiment, the hardness of the proximal connecting sections is greater than that of the proximal hanging sections.

In one embodiment, the proximal disk surface is basically parallel to the distal disk surface.

In one embodiment, the proximal supporting rod and the distal supporting rods connected with the corresponding proximal supporting rod are formed by bending one rod body, and the rod body is bent at the hanging end.

In one embodiment, the distal disk surface further includes a distal supporting structure with a number of grids; the distal supporting structure is radially deployed from the center of the distal disk surface along the radial direction; and the distal supporting rods are all connected with the distal supporting structure.

In one embodiment, the distal supporting structure includes a number of distal branches; the distal branches are connected with one another two by two to form the grids; and one end of each of part of the distal branches is gathered and connected at the center of the distal disk surface.

In one embodiment, the proximal disk surface further includes a proximal supporting structure with a number of grids; the proximal supporting structure is radially deployed from the center of the proximal disk surface along the radial direction; and the proximal supporting rods are all connected with the proximal supporting structure.

In one embodiment, the proximal supporting structure further includes proximal branches; the proximal branches are connected with one another two by two to form the grids; and one end of each of part of the proximal branches is gathered and connected at the center of the proximal disk surface.

In one embodiment, the sealing plate further includes a sealing film which covers at least one disk surface of the proximal disk surface and the distal disk surface.

In one embodiment, an outer circumferential edge of the sealing film extends out 1 mm to 15 mm in the radial direction relative to an outer circumferential edge of the disk surface covered by the sealing film.

In one embodiment, the radial deformability of the sealing plate is greater than that of the fixing frame and/or the axial deformability of the sealing plate is greater than that of the fixing frame.

In one embodiment, under an action of a same radial force, a radial length variation of the sealing plate is greater than that of the fixing frame; or under an action of the same radial force, a radial length change rate of the sealing plate is greater than that of the fixing frame; or under the action of the same axial force, a displacement of the sealing plate along an axial force direction is greater than that of the fixing frame along the axial force direction.

In the left atrial appendage occluder of the present disclosure, the supporting rods at the maximum-diameter portion of the sealing plate are relatively independent, the deformation of the maximum-diameter portion of the sealing plate may be increased to ensure that the outer edge of the sealing plate may adapt to various irregular opening portion shapes of left atrial appendages, and to achieve an optimal fitting and sealing effect. In addition, all the supporting rods of a framework may maintain a certain supporting force to resist a pulling force caused by its own movement of the left atrial appendage and a movement of the fixing frame, and to avoid long-term leakage, thereby reducing the risk of thrombosis and apoplexy.

DETAILED DESCRIPTION

For the purpose of making the description of a structure of a left atrial appendage occluder clearer, the present disclosure defines terms "distal end" and "proximal end". The above-mentioned terms are common used in the field of interventional medical devices. To be more specific, the "distal end" represents an end far away from an operator in a surgical process, and the "proximal end" represents an end close to the operator in the surgical process.

Figure 1:
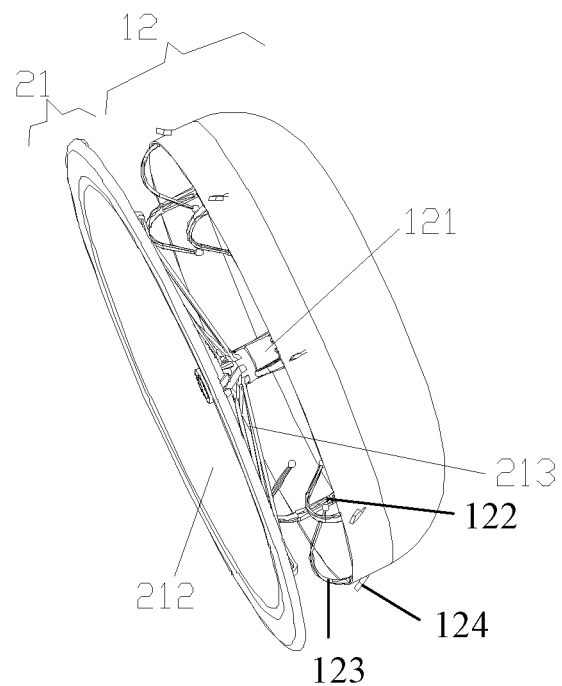
FIG. 1 is a schematic diagram of a left atrial appendage occluder provided by one embodiment of the present disclosure.

As shown in FIG. 1, a left atrial appendage occluder of one embodiment of the present disclosure includes a sealing plate 21 and a fixing frame 12 connected with the sealing plate 21. After the left atrial appendage occluder is implanted into a left atrial appendage, the fixing frame 12 is located in a cavity of the left atrial appendage and is closely fitted to the cavity wall to prevent the left atrial appendage occluder from falling off from the left atrial appendage; the sealing plate 21 seals an opening portion of the left atrial appendage to prevent a thrombus formed in a cavity of a left atrium from flowing into the left atrium, and/or to prevent blood flow from flowing from the left atrium into the cavity of the left atrial appendage.

The sealing plate 21 includes a framework 213 and a sealing film 212 arranged on the framework 213.

With reference to FIG. 1, FIG. 2, FIG. 3 and FIG. 4 at the same time, the framework 213 is overall of an umbrella-shaped skeletal structure. The framework 213 includes a proximal disk surface 2134 and a distal disk surface 2135. After the left atrial appendage occluder is implanted into the left atrial appendage, the proximal disk surface 2134 faces to the left atrium, and the distal disk surface 2135 faces to a cavity of the left atrial appendage.

The proximal disk surface 2134 includes a proximal seal head 2131 and multiple elastic proximal supporting rods 2137 radially arranged in a radial direction; the distal disk surface 2135 includes a distal seal head 2132 and multiple elastic distal supporting rods 2139 radially arranged in the radial direction; and a hanging end of each proximal supporting rod 2137 is connected with a hanging end of one distal supporting rod 2139 adjacent to the proximal supporting rod 2137.

To be more specific, one end of each proximal supporting rod 2137 is connected with the proximal seal head 2131, and the other end of the proximal supporting rod 2137 is radiated along the radial direction and then suspended; one end of each distal supporting rod 2139 is connected with the distal seal head 2132, and the other end of the distal supporting rod 2139 is radiated along the radial direction and then suspended. The proximal supporting rods 2137 and the distal supporting rods 2139 connected with the proximal supporting rods 2137 may be formed by bending one rod body 2138, and the rod body 2138 is bent at the hanging ends.

In this present disclosure, the proximal supporting rods 2137 of the proximal disk surface 2134 and the distal supporting rods 2139 of the distal disk surface 2135 of the sealing plate 21 all have hanging ends, and near the hanging ends, adjacent proximal supporting rods 2137 and adjacent distal supporting rods 2139 are relatively independent of each other, so that it is possible to increase the deformation of the sealing plate 21 here to ensure that the outer edge of the sealing plate 21 adapts to various irregular opening shapes of left atrial appendages to achieve an optimal fitting and sealing effect.

In addition, the sealing plate 21 has two disk surfaces, namely the proximal disk surface 2134 and the distal disk surface 2135. An interval is reserved between the two disk surfaces, but the two disk surfaces are still connected at the hanging ends. Preferably, except for the connection at the hanging ends, no other mutual connections are formed between the two disk surfaces. As the framework 213 is of the umbrella-shaped skeletal structure, all the proximal supporting rods 2137 and the distal supporting rods 2139 may maintain a certain amount of supporting force; when any one of the two disk surfaces is pulled, as the interval between the two disk surfaces provides a certain buffer effect, the pulling action on this disk surface may not directly act on the other disk surface, and the connected hanging ends further allow the non-pulled disk surface to play a role of pulling back the pulled disk surface to reduce a deformation amplitude of the pulled disk surface, thereby reducing poor sealing caused by disk surface deformation, and improving the occluding reliability of the left atrial appendage occluder.

To be more specific, when the proximal disk surface 2134 deforms under the pull of a delivery apparatus during delivery or releasing, the distal disk surface 2135 deforms very little and is essentially not affected by the pulling action due to the interval between the two disk surfaces, thereby guaranteeing the sealing effect; on the other hand, as the hanging ends of the two disk surfaces are connected, the distal disk surface 2135 may play a certain role of pulling back the proximal disk surface 2134 to avoid the position of the left atrial appendage occluder changing which will result in sealing failure, and even to avoid the left atrial appendage occluder falling off from the cavity of the left atrial appendage, due to an extremely large deformation of the proximal disk surface 2134 under the pull. For another example, if the distal disk surface 2135 is pulled by the fixing frame to adapt to the shape of the cavity of the left atrial appendage after the implantation of the left atrial appendage occluder is completed, the proximal disk surface 2134 basically may not be subjected to this pulling action, thus ensuring that the sealing plate still may be fitted to a tissue wall and maintain a sealing shape to guarantee the occluding effect; in addition, the proximal disk surface 2134 would further pull back the distal disk surface 2135 to a certain extent, to resist the pulling force caused by its own movement of the left atrial appendage and a movement of the fixing frame, and to avoid long-term leakage as far as possible, and to prevent the left atrial appendage occluder from falling into the cavity of the left atrial appendage.

In addition, the framework 213 of the sealing plate 21 is designed to be an umbrella-shaped skeleton, so that the structure is light in weight, and the metal content of the framework 213 may be reduced, and the amount of metal ions released into blood is decreased in a long term.

Figure 2:
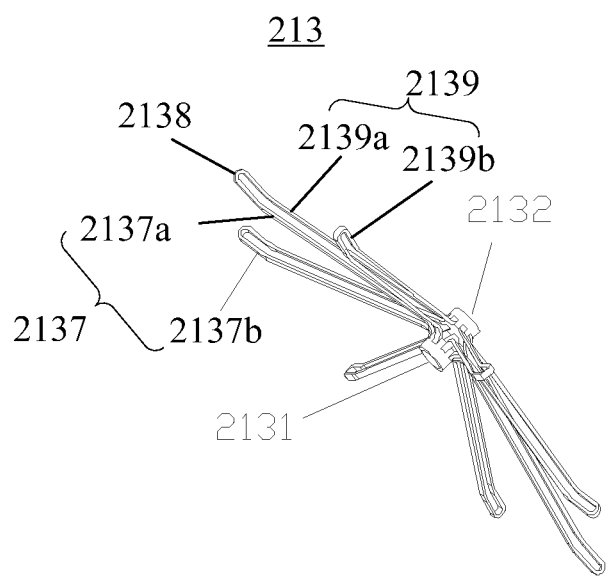
FIG. 2 is a schematic diagram of a framework of a sealing plate of the left atrial appendage occluder in FIG. 1.
Figure 3:
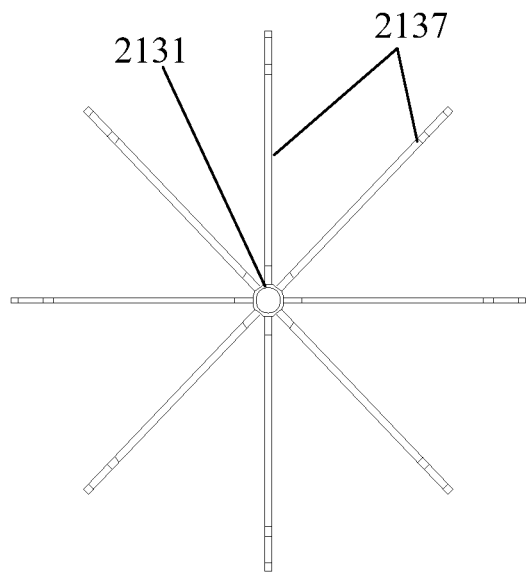
FIG. 3 is a front view of the framework in FIG. 2.
Figure 4:
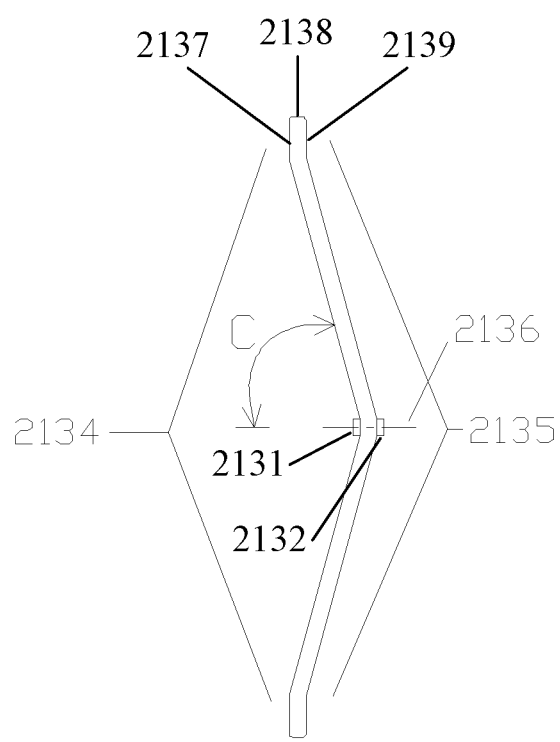
FIG. 4 is a side view of the framework as shown in FIG. 2.

As shown in FIGS. 2 through 4, the distal supporting rod 2139 includes a distal connecting section 2139a and a distal hanging section 2139b; one end of each distal connecting section 2139a is connected with the distal seal head 2132, and the other end of the distal connecting section 2139a is connected with one end of each distal hanging section 2139b; and the other end of each distal hanging section 2139b is connected with the hanging end of one proximal supporting rod 2137.

The proximal supporting rod 2137 includes proximal connecting section 2137a and a proximal hanging section 2137b; one end of each proximal connecting section 2137a is connected with the proximal seal head 2131, and the other end of the proximal connecting section 2137a is connected with one end of each proximal hanging section 2137b; and the proximal hanging section 2137b of the proximal supporting rod 2137 is connected with the distal hanging section 2139b of the distal supporting rod 2139. The rod body 2138 is located between the proximal disk surface 2134 and the distal disk surface 2135 to space the proximal disk surface 2134 from the distal disk surface 2135 to form an interval between the two disk surfaces, so that the sealing plate 21 is of a two-layer structure. The proximal seal head 2131 may be located in the center region of the proximal disk surface 2134. The distal seal head 2132 may be located in the center region of the distal disk surface 2135.

To be more specific, as shown in FIG. 3 and FIG. 4, in a naturally unfolded state, the proximal seal head 2131 and the distal seal head 2132 are axially aligned. Further, the axial line of the distal seal head 2132 and the axial line of the proximal seal head 2131 are both overlapped with the axial line 2136 of the framework 213. The proximal seal head 2131 and the distal seal head 2132 are arranged on the axial line 2136 of the framework 213 in a spaced manner. A projection of each distal supporting rod 2139 on the proximal disk surface 2134 is basically overlapped with one proximal supporting rod 2137 connected with this distal supporting rod 2139. Further, the distal hanging section 2139b is substantially perpendicular to the axial line of the distal seal head 2132. The proximal hanging section 2137b is substantially perpendicular to the axial line of the proximal seal head 2131. The proximal disk surface 2134 is substantially parallel to the distal disk surface 2135. It can be specifically understood that the proximal connecting sections 2137a of the proximal supporting rods 2137 are parallel to the distal connecting sections 2139a of the correspondingly connected distal supporting rods 2139, and the proximal hanging sections 2137b of the proximal supporting rods 2137 are parallel to the distal hanging sections 2139b of the correspondingly connected distal supporting rods 2139. It is stated above that one face of the framework 213 deforms when under stress, and the other face is affected little. Therefore, after the stress on the framework 213 disappears, the proximal supporting rods 2137 and the distal supporting rods 2139 return to a mutual-parallel naturally unfolded states.

In one embodiment, an included angle C between the proximal seal head 2131 and one proximal supporting rod 2137 is an acute angle, and an included angle between the distal seal head 2132 and one distal supporting rod 2139 is an acute angle. Further, the included angle C between the proximal supporting rod 2137 and the proximal seal head 2131 is 15 degrees to 90 degrees, and preferably 60 degrees to 85 degrees. Such setting allows the proximal disk surface 2134 and the distal disk surface 2135 to form a structure similar to a conical surface; the proximal seal head 2131 is located inside the structure, and the distal seal head 2132 is located at the vertex angle of the structure; and therefore, after the left atrial appendage occluder is implanted into the left atrial appendage, the sealing plate 21 may be better fitted to the opening portion of the left atrial appendage, and the distal disk surface 2135 may be fitted to the cavity wall, which is located at the opening portion of the left atrial appendage, of the left atrium.

In one embodiment, by way of material treatment, the hardness of the proximal hanging sections 2137b of the proximal supporting rods 2137 is greater than that of the distal hanging sections 2139b of the distal supporting rods 2139. As the distal hanging sections 2139b are closer to the opening portion of the left atrial appendage than the proximal hanging sections 2137b, distal hanging sections 2139b with lower hardness may reduce friction between the sealing plate 21 and the cavity wall, which is near to the opening portion of the left atrial appendage, of the left atrium, thereby avoiding a formation of hydropericardium or cardiac tamponade as much as possible. Further, the hardness of the distal connecting sections 2139a may be greater than that of the distal hanging sections 2139b in the distal disk surface 2135, so that it is able to reduce the friction between the distal hanging sections 2139b and a tissue wall to which the distal hanging sections 2139b are attached, and the distal connecting sections 2139a with the greater hardness ensure that the occluding shape of the disk surface is not liable to deform under the pull of the disk surface. Similarly, the hardness of the proximal connecting sections 2137a also may be greater than that of the proximal hanging sections 2137b in the proximal disk surface 2134.

At least two proximal supporting rods 2137, preferably 6 to 8 proximal supporting rods 2137, are provided, thereby ensuring that there are sufficient contact pivots and area between the framework 213 and the cavity wall at the opening portion of the left atrial appendage and guaranteeing a stable sealing effect.

In some embodiments, the proximal seal head 2131 and all the proximal supporting rods 2137 are integrated- or integratedly-formed by cutting.

In some embodiments, the distal seal head 2132 and all the distal supporting rods 2139 are integratedly-formed by cutting.

In some embodiments, the whole framework 213 may be formed by cutting a metal tube into a preset pattern and then shaped by a thermal treatment. To be more specific, the framework 213 may be formed by cutting a metal (preferably nickel-titanium material) tube with a diameter of 0.3 mm to 5 mm into a certain pattern, and then shaped by thermal treatment shaping. The proximal seal head 2131 and the proximal supporting rods 2137 are integrated, as well as the distal seal head 2132 and the distal supporting rods 2139. In some other embodiments, the framework 213 also may be formed by carrying out thermal treatment on multiple metal wires and then fixedly connecting the metal wires. The metal wires are preferably made of a nickel-titanium material. For example, two ends of multiple metal wires with the diameter of 0.05 mm to 0.8 mm or two ends of multiple flat metal wires with the sectional area of 0.03 mm×0.8 mm are fixed by welding, riveting, adhering, or other manners, as desired, to form the proximal seal head 2131 and the distal seal head 2132, and then the metal wires are shaped by a thermal treatment to obtain the framework 213 with corresponding shape.

Figure 5:
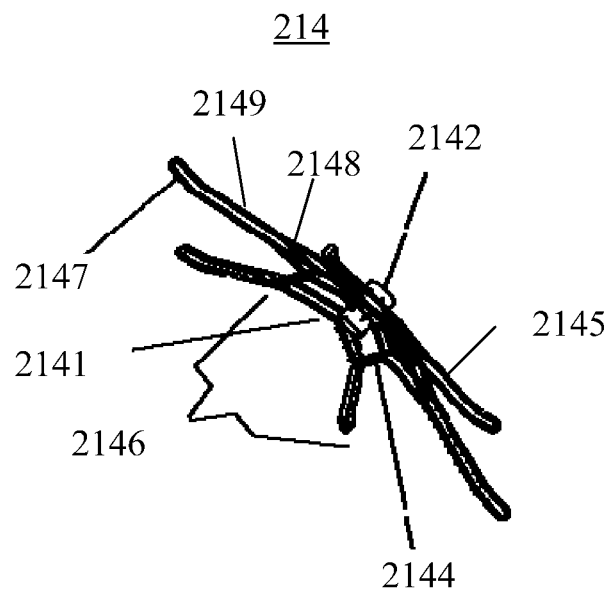
FIG. 5 is a schematic diagram of a framework of a sealing plate of a left atrial appendage occluder provided by another embodiment of the present disclosure.
Figure 6:
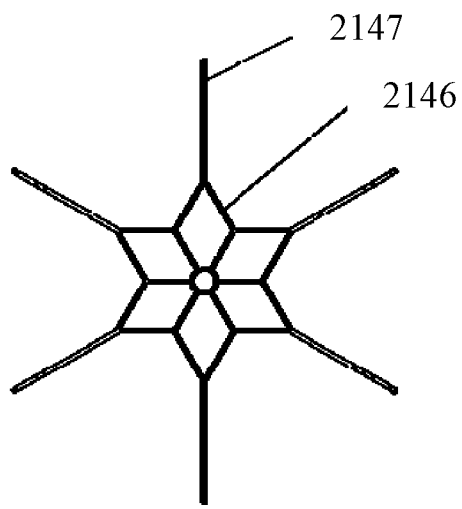
FIG. 6 is a front view of the framework in FIG. 5.

FIG. 5 and FIG. 6 illustrate a framework 214 provided by another embodiment. This framework 214 also includes a proximal disk surface 2144, a distal disk surface 2145 and other structures. The proximal disk surface 2144 includes a proximal seal head 2141 and proximal supporting rods 2147; the distal disk surface 2145 includes a distal seal head 2142 and distal supporting rods 2149. The difference from the framework 213 in the above embodiment is that the distal disk surface 2145 in this embodiment also includes a distal supporting structure 2148 with multiple grids; the distal supporting structure 2148 radiates from the center of the distal disk surface 2145 along a radial direction; and the multiple distal supporting rods 2149 are all connected with the distal supporting structure 2148.

Further, the distal supporting structure 2148 includes multiple distal branches; and the multiple distal branches are connected with one another two by two to form the multiple grids, wherein one end of each of part of the multiple distal branches is gathered and connected at the center of the distal disk surface 2145.

Further, the proximal disk surface 2144 also includes a proximal supporting structure 2146 with multiple grids; the proximal supporting structure 2146 radiates from the center of the proximal disk surface 2144 along the radial direction; and the multiple proximal supporting rods 2147 are all connected with the proximal supporting structure 2146. The proximal supporting structure 2146 includes multiple proximal branches; and the multiple proximal branches are connected with one another in a two by two manner to form the multiple grids, wherein one end of each of part of the multiple proximal branches is gathered and connected at the center of the proximal disk surface 2144. It should be understood that at least one of the disk surface of the proximal disk surface 2144 and the distal disk surface 2145 has the above-mentioned supporting structure. In addition, the proximal supporting structure 2146 and the distal supporting structure 2148 are located in the center region of the framework 214, and are both separated from the other in a disconnected state, respectively, to maintain relative independence, so that strength of the supporting force of the sealing plate 21 is enhanced at the center region, where the supporting structure is located, to ensure that the sealing plate 21 has a sufficient supporting force and will not be pulled by the fixing frame 12 into the left atrial appendage. On the other hand, the proximal supporting rods 2137 and the distal supporting rods 2139 still may be well fitted to the irregular shape of the opening portion of the left atrial appendage at the hanging ends, thereby achieving an optimal sealing effect.

Figure 7:
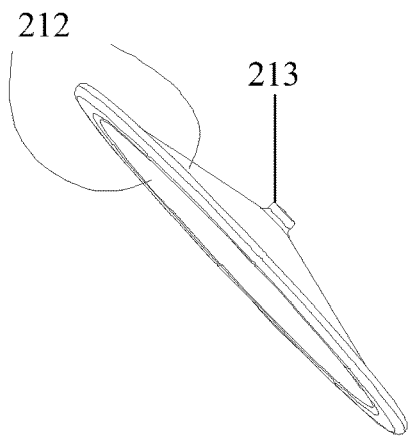
FIG. 7 is a schematic diagram of a sealing plate of a left atrial appendage occluder provided by another embodiment of the present disclosure.

As shown in FIG. 1 and FIG. 7, the sealing film 212 may be a single-layer film covering at least one disk surface of the framework 213, specifically covering the proximal disk surface 2134 and/or the distal disk surface 2135 of the framework 213. When the proximal disk surface 2134 is covered, the size of the sealing film 212 allows it to cover the whole proximal disk surface 2134 or is slightly larger than that of the proximal disk surface 2134, for example, the sealing film 212 extends out 1 mm to 15 mm in the radial direction relative to the outer circumferential edge of the proximal disk surface 2134, and the radial extending portion may be impending freely or extend towards the distal disk surface 2135 to cover it. When the distal disk surface 2135 is covered, the size of the sealing film 212 allows it to cover the whole distal disk surface 2135 or is slightly larger than that of the distal disk surface 2135. For example, the sealing film 212 extends out 1 mm to 15 mm in the radial direction relative to the outer circumferential edge of the distal disk surface 2135, and the radial extending portion may be impending freely or extend towards the proximal disk surface 2134 to cover it.

The sealing film 212 is generally made of a macromolecular material such as PET (polyethylene terephthalate), or PTFE (polytetrafluoroethylene), or a silica gel material, and also other thin film materials with biocompatibility and physical property which meet the requirements, as desired. A fixed connection between the sealing film 212 and the framework 213 may be realized by suturing, adhering or hot melting.

The sealing film 212 is arranged on the sealing plate 21, so that the sealing film 212 is a portion, which directly contacts with a tissue at the opening portion of the left atrial appendage, of the sealing plate 21, thereby reducing abrasion between a metal material and the tissue at the opening portion, lowering the risk of hydropericardium or cardiac tamponade caused by tissue abrasion, and promoting endothelialization at the junction between the sealing plate 21 and the tissue to enhance the sealing effect. In addition, the whole framework 213 is covered by the sealing film 212, so that the amount of metal ions released by the framework 213 entering the blood and the tissue may be reduced, to reduce a risk of inflammation.

As shown in FIG. 1, the fixing frame 12 includes multiple supporting members 122; ends of the multiple supporting members 122 are connected together. For example, these ends may be fixedly connected by welding or riveting, and the other end of each of the multiple supporting members 122 extends out in a radiated manner; the multiple supporting members 122 cooperate to form an umbrella-shaped structure; and each supporting member 122 includes a hanging supporting section 123. The fixing frame may be made by cutting, for example, the fixing frame may be obtained by cutting a metal tube; the metal tube may be made of a shape memory material, for example a nickel-titanium alloy. In some embodiments, anchor bars 124 also may be formed on the hanging supporting sections 123; the anchor bars 124 are inserted into the cavity wall of the left atrial appendage to connect the fixing frame with the cavity wall. After the left atrial appendage occluder, implanted into a human body, is released and unfolded, the fixing frame 12 is placed into the cavity of the left atrial appendage and attached to the cavity wall of the left atrial appendage; and the sealing plate 21 covers the opening of the left atrial appendage.

The sealing plate 21 is connected with a proximal end 121 of the fixing frame 12 through the distal seal head 2132 of the framework 213, and the connection between the sealing plate 21 and the fixing frame 12 may be realized in a welding, riveting, adhering or interference fit way.

Further, in some embodiments, the left atrial appendage occluder also may include a connection member for connecting the sealing plate 21 with the fixing frame 12. The connection member is flexible and elastic. One side of the connection member is connected with the distal seal head 2132, and the other side of the connection member is connected with the proximal end 121 of the fixing frame 12. This connection may be realized in a welding, riveting, adhering or interference fit way.

The connection member may change its length to adjust a distance between the sealing plate 21 and the fixing frame 12 under the action of an external force, for example under the pulling action of the sealing plate 21 and/or the fixing frame 12, by virtue of its flexibility and elasticity, and also may adjust an angle between the sealing plate 21 and the fixing frame 12. Therefore, the left atrial appendage occluder provided by the present disclosure may meet implantation requirements of left atrial appendages in different shapes such as, for example, a chicken wing shape and a conical shape.

Further, the radial deformability of the sealing plate 21 of the left atrial appendage occluder is greater than that of the fixing frame 12 and/or the axial deformability of the sealing plate 21 is greater than that of the fixing frame 12. To be more specific, under the action of the same radial force, a radial length variation of the sealing plate 21 is greater than that of the fixing frame 12; or under the action of the same radial force, a radial length change rate of the sealing plate 21 is greater than that of the fixing frame 12; or under the action of the same axial force, a displacement of the sealing plate 21 along an axial force direction is greater than that of the fixing frame along the axial force direction.

Radial length changes of the fixing frame and the sealing plate under the action of the same radial force may be respectively tested by a flat plate method. For example, with reference to FIG. 8 and FIG. 9, the left atrial appendage occluder may be tested by the flat plate method.

Figure 8:
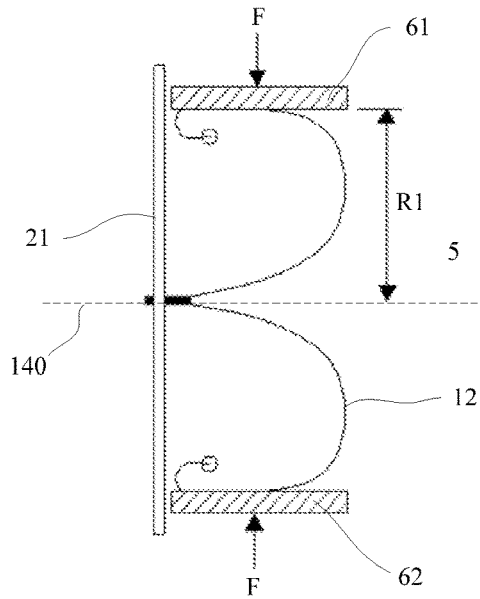
FIG. 8 is a schematic diagram of a test method of the radial deformability of a fixing frame of the left atrial appendage occluder in FIG. 1.

With reference to FIG. 8, first, on the premise that the sealing plate 21 maintains a freely unfolded state, radial acting forces F are applied to the fixing frame 12 by two parallel flat plates 61 and 62. To be more specific, the parallel flat plates 61 and 62 are respectively placed on two opposite sides of a diameter of the fixing frame 12, and two radial acting forces F with the same size and opposite directions are respectively applied to the flat plates 61 and 62 along the diameter. The diameter of the fixing frame 12 penetrates through and is perpendicular to a central axial line 140. The two parallel flat plates 61 and 62 maintain a mutually parallel state in the whole test process, namely the flat plates are parallel to the central axial line 140 all the time in the test process. And any one of the flat plates at least covers a contour with maximum radius of the fixing frame 12, and preferably the flat plate covers the whole fixing frame 12 in a direction parallel to the central axial line 140. In the naturally unfolded state, the radial lengths of portions, where the flat plates are loaded, of the fixing frame 12 are R1, the radial length variation of the fixing frame 12, under the action of the radial forces F, is a radial length difference obtained before and after radial compression, and may be expressed by $\Delta R1$, so that the radial length change rate is $\Delta R1/R1$. In order to guarantee that each of the flat plates itself is not deformed in a radial force applying process, and the radial forces can be evenly applied to all portions of the flat plates, and a thickness of the flat plates is at least 5 mm.

Figure 9:
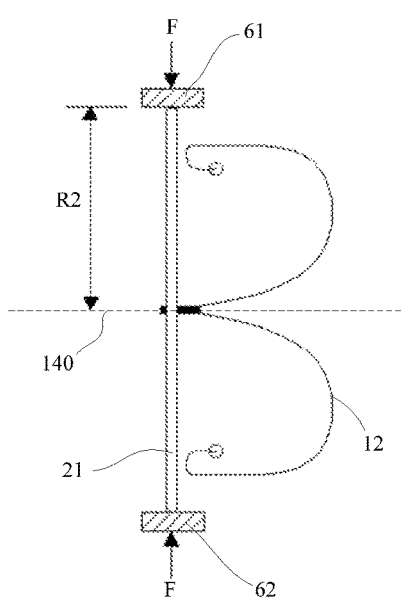
FIG. 9 is a schematic diagram of a test method of the radial deformability of a sealing plate of the left atrial appendage occluder in FIG. 1.

With reference to FIG. 9, the sealing plate 21 is tested by the flat plate test method as above, namely the same radial acting forces F, which refers to the same the size, direction and acting time, are adopted. On the premise that the sealing plate 21 is naturally unfolded, the radial length variation $\Delta R2$ or the radial length change rate $\Delta R2/R2$ of the sealing plate 21 is tested; and at the moment, a contour with maximum radius of the sealing plate 21 is located at the edges of the double plates. Based on the above test condition, under the action of the same radial force, the radial length variation $\Delta R2$ of the sealing plate 21 of the left atrial appendage occluder according to the embodiment of the present disclosure is greater than the radial length variation $\Delta R1$ of the fixing frame 12; or the radial length change rate $\Delta R2/R2$ of the sealing plate 21 of the left atrial appendage occluder according to the embodiment of the present disclosure is greater than the radial length change rate $\Delta R1/R1$ of the fixing frame 12.

After the left atrial appendage occluder is implanted into a human body, a situation where the implantation location may be improperly selected, may occur. For example, if the fixing frame extends too deep into the cavity of the left atrial appendage, an axial length of the occluder in the naturally unfolded state would be shorter than a relative distance between the fixing frame and the sealing plate after the implantation, which will lead to a mutual traction between the fixing frame and the sealing plate. Or, the implanted occluder would move together with the heart, but the implanted occluder and the heart have different amplitudes or directions of motion, which may lead to the mutual traction between the fixing frame and the sealing plate. Generally, the fixing plate and the sealing plate pull each other through the connection member.

When the fixing frame is pulled by the sealing plate, as the fixing frame is fixed in the cavity of the left atrial appendage through a radial supporting force surrounding a circumferential region of the central axial line 140, the fixing frame is attached to the circumferential region of the cavity of the left atrial appendage to resist this pulling acting force. Therefore, the fixing frame will be radially deformed under the axial acting force and the fixing frame will separate from the cavity wall of the left atrial appendage if the pulling acting force is large enough, and then the left atrial appendage occluder would fall off, which will cause an implantation failure. When the sealing plate is pulled by the fixing frame, the sealing plate has the disk surface structure and is connected with the connection member through the disk surface, so that the axial pulling on the sealing plate would also lead to a radial deformation of the sealing plate.

Therefore, when the fixing frame and the sealing plate pull each other, the one who is easily deformed in the radial direction will be pulled by the other one. For example, under the same radial acting force, as the radial length variation of the fixing frame according to the embodiment of the present disclosure is less than that of the sealing plate, or the radial length change rate of the fixing frame according to the embodiment of the present disclosure is less than that of the sealing plate, in the mutual traction, the fixing frame would dominate the traction and pull the sealing plate to make the sealing plate deform towards the fixing frame direction (or towards the distal end). Such deformation enables the sealing plate to be closer to a left atrial wall at an opening of the left atrial appendage than that of the sealing plate in the naturally unfolded state, which enhances a sealing effect between the sealing plate and the opening of the left atrial appendage and avoids an interval between the sealing plate and the left atrial wall, so that it can prevent apoplexy or systematic embolism caused by blood flowing into the cavity of the left atrial appendage and a thrombus flowing into a left atrium through the interval. In addition, the fixing frame dominates the traction so that the fixing frame will not easily separate from the cavity wall of the left atrial appendage under the pull of the sealing plate, and the occluder will be better fixed in the left atrial appendage to avoid falling off from the left atrial appendage.

Figure 10:
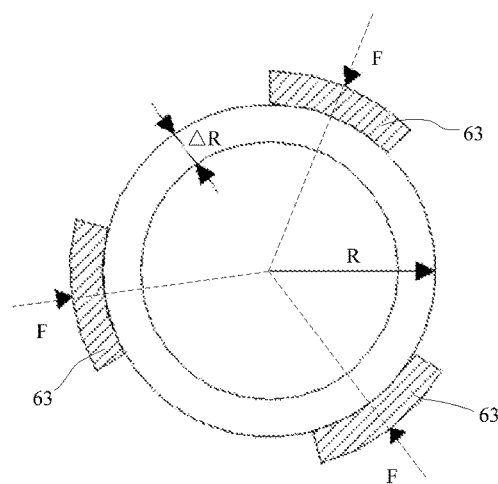
FIG. 10 is a schematic diagram of another specific test method of the radial deformability of the sealing plate/fixing frame of the left atrial appendage occluder in FIG. 1.

The above flat plate method is only an example method, and not a limitation of the present disclosure. A person of ordinary skill in the art can adopt any other proper method, equivalent to the flat plate method, for testing. For example, a test method that the radial acting force is evenly applied to a tested component in a circumferential direction may be utilized. To be more specific, with reference to FIG. 10, three arc-shaped plates 63 may be uniformly disposed, in the same circumferential direction, on the contour with maximum radius of the tested component (the fixing frame or the sealing plate). During the test, radial acting forces F are simultaneously applied to the above arc-shaped plates 63 along a radial direction to test a variation or a change rate of a radial length R of the tested component. Similarly, in order to apply the radial force evenly, a thickness of the arc-shaped plates is at least 5 mm. Furthermore, the left atrial appendage occluder may be tested by a radial supporting force tester RX550-100 of the Machine Solution Inc (MSI) Company.

In addition, when one portion of the tested component (the fixing frame or the sealing plate) is restricted, the axial deformability of the tested component is expressed by testing an axial displacement (along the direction of the central axial line 140) of the tested component under an action of the same axial force. In the test method as above, the above restriction is equidimensional restriction, that is to say, in the restriction process, the tested component does not elastically deform or deforms a little, which may be ignored; and in addition, the axial acting force is applied to a position, where no elastic deformation occurs, of the tested component. For example, the same axial acting forces are applied to end portions, which are connected with the connection member, of the tested component, and the axial displacement of the tested component is used to express its own deformability, and the axial displacement of the component here refers to a position, where the axial acting force is applied, of the tested component, and the left atrial appendage meets the condition that the axial displacement of the fixing frame is less than that of the sealing plate. Detailed test methods will be described below according to the structure of the left atrial appendage occluder. During the testing, the fixing frame and the sealing plate are independently tested, for example, only a single fixing frame or a single sealing plate is tested at each time.

Figure 11:
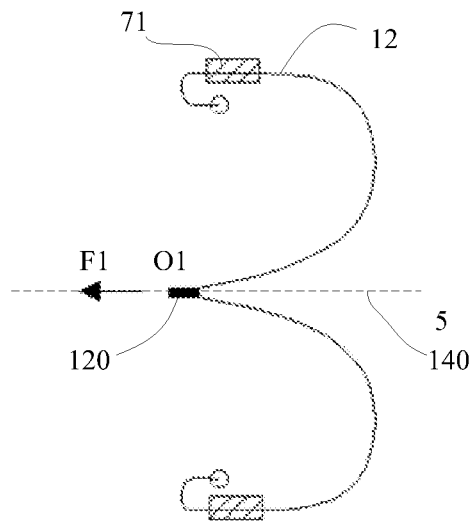
FIG. 11 is a schematic diagram of a first test method of the axial deformability of the fixing frame of the left atrial appendage occluder in FIG. 1.

With reference to FIG. 11, during a test of the fixing frame 12, a clamping portion, where the fixing frame 33 is clamped by an annular clamping member 71 along a circumferential direction, is the contour with maximum radius of the fixing frame 12. The annular clamping member 71 surrounds, and is perpendicular to, the central axial line 140. In a clamping process, the radial size of the clamping portion of the fixing frame 12 is basically equal to that of a fixing frame 33 in the naturally unfolded state, so that the elastic deformation may be ignored. An axial acting force F1, along the central axial 140 and towards the direction of the sealing plate 21, is applied to the end portion 120, which is connected with the connection member, of the fixing frame 12, and the end portion 120 does not elastically deform in the process of applying the axial acting force F1. Measuring an axial displacement $\Delta O1$ of a projection O1 of the end portion 120 on the central axial line 140 under the F1. The axial displacement $\Delta O1$ is used to express the deformation (or the deformability) of the fixing frame 12 in the first axial deformability test method, and the state of the clamping member 71 itself stays unchanged during the action of the axial acting force F1.

After the left atrial appendage occluder is implanted into the human body, and under a condition that one portion, such as the maximum contour, of the fixing frame is clamped, it can be seen that the tested axial displacement, under the action of an axial acting force, represents the axial deformability of the fixing frame, which is under the pull of the sealing plate and the restricting action of the cavity of the left atrial appendage. Under the same axial acting force, the larger the axial displacement $\Delta O1$ is, the easier it is for the fixing frame to be pulled and deformed.

Figure 12:
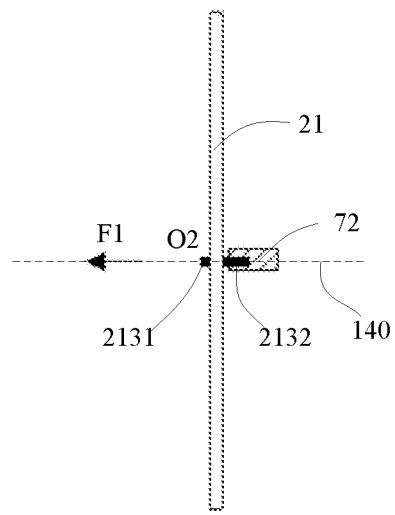
FIG. 12 is a schematic diagram of a first test method of the axial deformability of the sealing plate of the left atrial appendage occluder in FIG. 1.

With reference to FIG. 12, during a test of the sealing plate 21, distal seal head 2132 of the sealing plate 21 is clamped by the clamping member 72; and the axial acting force F1, applied to the proximal seal head 2131 of the sealing plate 21 along the central axial line 140 and towards a direction away from the fixing frame 12, is equal to the text of the fixing frame 12. Measuring another axial displacement $\Delta O2$ of a projection O2 of the proximal seal head 2131 on the central axial line 140 under the F1 is also performed. The axial displacement $\Delta O2$ is used to express the axial deformation (or the deformability) of the sealing plate 21 in the first axial deformability test method.

After the left atrial appendage occluder is implanted into the human body, and under a condition that one portion, such as the distal seal head 2132, of the sealing plate is clamped, it can be seen that the tested axial displacement under the action of the axial acting force F1 represents the axial deformability of the sealing plate 21, which is under the pull of the fixing frame 12 and the restricting action of a wall of the opening portion of the left atrial appendage. Under the same axial acting force, the larger the axial displacement $\Delta O2$ is, the easier it is for the sealing plate 31 to be pulled and deformed. It is tested that, under the action of the same axial force, the axial displacement $\Delta O1$ of the fixing frame is less than the axial displacement $\Delta O2$ of the sealing plate. It can be understood that when the fixing frame and the sealing plate pull each other, the one who has a larger axial displacement will be pulled by the other one. For example, under the same axial acting force, as the axial displacement of the fixing frame according to the embodiment of the present disclosure is less than that of the sealing plate, the fixing frame would dominate the traction and pull the sealing plate during the traction to make the sealing plate deform towards a direction of the fixing frame (or towards the distal end). Such deformation enables the sealing plate to be more close to the left atrial wall at the opening of the left atrial appendage than that of the sealing plate in the naturally unfolded state, which enhances a sealing effect between the sealing plate and the opening of the left atrial appendage and avoids an interval between the sealing plate and the left atrial wall, so that it can prevent blood from flowing into the cavity of the left atrial appendage and a thrombus from flowing into a left atrium through the interval. In addition, the fixing frame dominates the traction so that the fixing frame will not easily separate from the cavity wall of the left atrial appendage under the pull of the sealing plate, and the occluder will be better fixed in the left atrial appendage to avoid falling off of the left atrial appendage.

Figure 13:
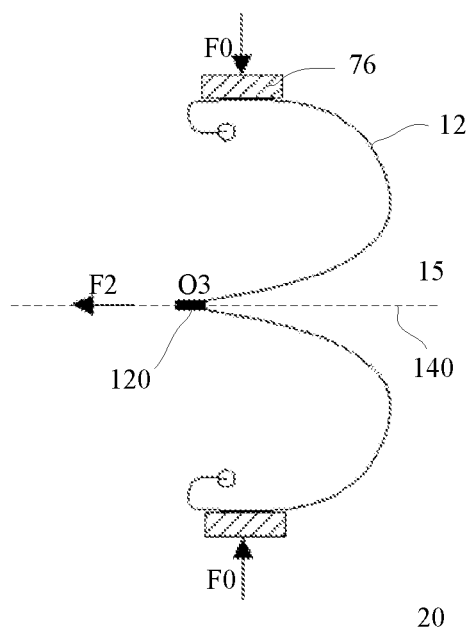
FIG. 13 is a schematic diagram of a second test method of the axial deformability of the fixing frame of the left atrial appendage occluder in FIG. 1.

A second axial deformability test method may be further adopted. With reference to FIG. 13, during a test of the fixing frame 12, a clamping portion, where the fixing frame 33 is clamped by an annular clamping member 76 along a circumferential direction, has the contour with maximum radius of the fixing frame 12. The annular clamping member surrounds and is perpendicular to the central axial line 140. In a clamping process, the radial size of the clamping portion of the fixing frame 12 is smaller than that of a fixing frame 12 in the naturally unfolded state. The clamping portion of the fixing frame 12 is compressed in the radial direction, for example, the maximum radial length after compressed is 80 percent of the maximum radial length before it is compressed. Of course, other compression ratios may be adopted, as desired, but are not listed here for the sake of brevity. For example, a radial force F0 may be applied to the annular clamping member 76 to compress the fixing frame 12 in the radial direction. An axial acting force F2 is applied to the end portion 120, where the fixing frame 12 is connected with the connection member, and the end portion 120 does not deform ender the axial acting force F2 which is along the central axial line 140 and towards the direction of the sealing plate 21. Measuring an axial displacement $\Delta O3$ of a projection O3 of the end portion 120 on the central axial line 140 under the F2, the axial displacement $\Delta O3$ is used to express the deformation (or the deformability) of the fixing frame 12 in the second axial deformability test method.

After the left atrial appendage occluder is implanted into a human body, and under a condition that one portion, such as the maximum contour, of the fixing frame 12 is clamped, it can be seen that the tested axial displacement under the action of the axial acting force represents the deformability of the fixing frame 12, which is under the pull of the sealing plate 21 and the restricting action of the cavity of the left atrial appendage. Under the same axial acting force, the larger the axial displacement $\Delta O3$ is, the easier it is for the fixing frame 12 to be pulled and deformed.

Figure 14:
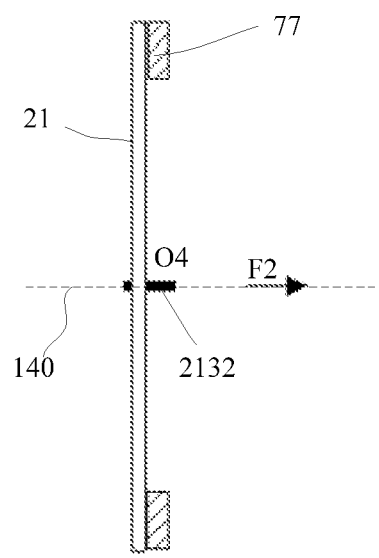
FIG. 14 is a schematic diagram of a second test method of the axial deformability of the sealing plate of the left atrial appendage occluder in FIG. 1.

With reference to FIG. 14, the sealing plate 21 includes a distal seal head 2132; and the connection member is connected with the distal seal head 2132. During an independent test of the sealing plate 21, an annular fixing member 77 abuts a disk surface, which is towards the fixing frame 12 and located at the maximum edge of the sealing plate 31. Meanwhile, the axial acting force F2, along the central axial line 140 and towards a direction of the fixing frame 12, is applied to the distal seal head 2132. Under the axial acting force F2, a position where the disk surface is abutted maintains unchanged along the direction of the central axial line 140 due to the annular fixing member 77, thereby testing a projection displacement 404 of the distal seal head 2132 on the central axial line 140.

It can be seen from the above that, after the left atrial appendage occluder is implanted into the human body, a portion of the sealing plate is blocked by the cavity wall of the left atrium at the opening portion of the left atrial appendage, wherein the portion of the sealing plate faces to the fixing frame and is at least the edge of the sealing plate with maximum radius. Therefore, during the above test of the sealing plate, and under a condition that the position, abutted by the annular fixing member 77, of the disk surface, maintains unchanged along the direction of the central axial line 140, and an axial displacement, tested under the action of the axial force, of the sealing plate represents the deformability of the sealing plate pulled by the fixing frame at the opening of the left atrial appendage after the occluder is implanted into the human body. Under the same axial acting force, the larger the axial displacement $\Delta O4$ is, the easier the sealing plate will be pulled and deformed.

It is tested that, under the action of the same axial force (F2), the axial displacement $\Delta O3$ of the fixing frame is less than the axial displacement $\Delta O4$ of the sealing plate. It can be understood that when the fixing frame and the sealing plate pull each other, the one who has a larger axial displacement will be pulled by the other one. For example, under the same axial acting force as the axial displacement of the fixing frame, according to the embodiment of the present disclosure, is less than that of the sealing plate, the fixing frame would dominate the traction and pull the sealing plate during the traction to make the sealing plate deform towards a direction of the fixing frame (or towards the distal end). Such deformation enables the sealing plate to be more close to the left atrial wall at the opening portion of the left atrial appendage than that of the sealing plate in the naturally unfolded state, which enhances a sealing effect between the sealing plate and the opening of the left atrial appendage and avoids an interval between the sealing plate and the left atrial wall, so that it can prevent blood from flowing into the cavity of the left atrial appendage and prevent a thrombus from flowing into a left atrium through the interval. In addition, the fixing frame dominates the traction so that the fixing frame will not easily separate from the cavity wall of the left atrial appendage under the pull of the sealing plate, and the occluder will be better fixed in the left atrial appendage to avoid falling off of the left atrial appendage.

All technical features of the above embodiments may be randomly combined. In order to simplify the description, not all possible combinations of the respective technical features in the embodiments are described. However, the combinations of these technical features shall fall within the scope described in the description in case of no contradictions.

The above embodiments only express a few of embodiments of the present disclosure, and their descriptions are relatively specific and detailed, but shall not be regarded as limitations to the scope of the patent for the present disclosure. It should be noted that persons of ordinary skill in the art can further make a number of deformations and improvements without departing from the idea of the present disclosure, and these deformations and improvements shall all fall within the protection scope of the present disclosure. Therefore, the protection scope of the patent for the present disclosure shall be based on attached claims.

The invention claimed is:

1. A left atrial appendage occluder, comprising:
   a sealing plate and a fixing frame connected with the sealing plate, wherein the sealing plate comprises a proximal disk surface and a distal disk surface;
   the proximal disk surface comprises a proximal seal head and a plurality of elastic proximal supporting rods arranged in a radiated manner in a radial direction, wherein one end of each proximal supporting rod is connected with the proximal seal head, and the other end of each proximal supporting rod is radiated in the radial direction and has a hanging end;
   the distal disk surface comprises a distal seal head and a plurality of elastic distal supporting rods arranged in a radiated manner in the radial direction, wherein one end of each distal supporting rod is connected with the distal seal head, and the other end of each distal supporting rod is radiated in the radial direction and has a hanging end; and
   a hanging end of each proximal supporting rod is connected with a hanging end of a respective one of the distal supporting rods adjacent to the proximal supporting rod,
   wherein each distal supporting rod comprises a distal connecting section and a distal hanging section, one end of each distal connecting section is connected with the distal seal head, and the other end of each distal connecting section is connected with one end of each distal hanging section; the other end of each distal hanging section is connected with the hanging end of one proximal supporting rod, and the distal hanging sections are substantially perpendicular to an axial line of the distal seal head, and
   wherein a hardness of the distal connecting section is greater than that of the distal hanging section.

2. The left atrial appendage occluder according to claim 1, wherein the proximal seal head and the distal seal head are axially aligned; and
   substantially all of a projection of each distal supporting rod on the proximal disk surface is overlapped with one proximal supporting rod connected with the distal supporting rod.

3. The left atrial appendage occluder according to claim 1, wherein the proximal seal head and all of the proximal supporting rods are formed by integrated cutting, and/or the distal seal head and all of the distal supporting rods are formed by integrated cutting, and/or the proximal supporting rods and the distal supporting rods connected with the proximal supporting rods are formed by integrated bending of one rod body.

4. The left atrial appendage occluder according to claim 1, wherein a proximal connection included angle between the proximal seal head and one proximal supporting rod is an acute angle, and a distal connection included angle between the distal seal head and one distal supporting rod is an acute angle.

5. The left atrial appendage occluder according to claim 4, wherein the proximal connection included angle between the proximal seal head and one proximal supporting rod is in a range from 15 degrees to 90 degrees, and the distal connection included angle between the distal seal head and one distal supporting rod is in a range from 15 degrees to 90 degrees.

6. A left atrial appendage occluder, comprising:
   a sealing plate and a fixing frame connected with the sealing plate, wherein the sealing plate comprises a proximal disk surface and a distal disk surface;
   the proximal disk surface comprises a proximal seal head and a plurality of elastic proximal supporting rods arranged in a radiated manner in a radial direction, wherein one end of each proximal supporting rod is connected with the proximal seal head, and the other end of each proximal supporting rod is radiated in the radial direction and has a hanging end;
   the distal disk surface comprises a distal seal head and a plurality of elastic distal supporting rods arranged in a radiated manner in the radial direction, wherein one end of each distal supporting rod is connected with the distal seal head, and the other end of each distal supporting rod is radiated in the radial direction and has a hanging end; and
   a hanging end of each proximal supporting rod is connected with a hanging end of a respective one of the distal supporting rods adjacent to the proximal supporting rod,
   wherein each distal supporting rod comprises a distal connecting section and a distal hanging section, one end of each distal connecting section is connected with the distal seal head, and the other end of each distal connecting section is connected with one end of each distal hanging section; the other end of each distal hanging section is connected with the hanging end of one proximal supporting rod, and the distal hanging sections are substantially perpendicular to an axial line of the distal seal head,
   wherein each proximal supporting rod comprises a proximal connecting section and a proximal hanging section, one end of each proximal connecting section is connected with the proximal seal head, and the other end of each proximal connecting section is connected with one end of each proximal hanging section, and the proximal hanging section of each proximal supporting rod is connected with a respective one distal hanging section adjacent to the proximal hanging section, and
   wherein a hardness of each proximal connecting section is greater than that of each proximal hanging section.

7. The left atrial appendage occluder according to claim 1, wherein the proximal disk surface is substantially parallel to the distal disk surface.

8. The left atrial appendage occluder according to claim 1, wherein each of the proximal supporting rod and each of the distal supporting rod connected with the corresponding proximal supporting rod are formed by bending one rod body, and the rod body is bent at the hanging end.

9. The left atrial appendage occluder according to claim 1, wherein the distal disk surface further comprises a distal supporting structure with a plurality of grids;
   the distal supporting structure is radially deployed from a center of the distal disk surface along the radial direction; and
   the distal supporting rods are each connected with the distal supporting structure.

10. The left atrial appendage occluder according to claim 9, wherein the distal supporting structure comprises a plurality of distal branches;
    the distal branches are connected with one another two by two to form the grids; and
    one end of each of the distal branches is gathered and connected at the center of the distal disk surface.

11. The left atrial appendage occluder according to claim 9, wherein the proximal disk surface further comprises a proximal supporting structure with a plurality of grids;
    the proximal supporting structure is radially deployed from the center of the proximal disk surface along the radial direction; and
    the proximal supporting rods are each connected with the proximal supporting structure.

12. The left atrial appendage occluder according to claim 11, wherein the proximal supporting structure further comprises proximal branches;
    the proximal branches are connected with one another two by two to form the grids; and
    one end of each of the proximal branches is gathered and connected at the center of the proximal disk surface.

13. The left atrial appendage occluder according to claim 1, wherein the sealing plate further comprises a sealing film which covers at least one disk surface of the proximal disk surface and the distal disk surface.

14. A left atrial appendage occluder, comprising:
    a sealing plate and a fixing frame connected with the sealing plate, wherein the sealing plate comprises a proximal disk surface, a distal disk surface, and a sealing film which covers at least one disk surface of the proximal disk surface and the distal disk surface, wherein an outer circumferential edge of the sealing film extends out 1 mm to 15 mm in the radial direction relative to an outer circumferential edge of the disk surface covered by the sealing film,
    the proximal disk surface comprises a plurality of elastic proximal supporting rods arranged in a radiated manner in a radial direction;
    the distal disk surface comprises a plurality of elastic distal supporting rods arranged in a radiated manner in the radial direction; and
    a hanging end of each proximal supporting rod is connected with a hanging end of a respective one of the distal supporting rods adjacent to the proximal supporting rod.

15. The left atrial appendage occluder according to claim 1, wherein a radial deformability of the sealing plate is greater than that of the fixing frame and/or an axial deformability of the sealing plate is greater than that of the fixing frame.

16. The left atrial appendage occluder according to claim 15, wherein under an action of a same radial force, a radial length variation of the sealing plate is greater than that of the fixing frame; or
    under the action of the same radial force, a radial length change rate of the sealing plate is greater than that of the fixing frame; or
    under the action of the same axial force, a displacement of the sealing plate along an axial force direction is greater than that of the fixing frame along the axial force direction.

17. The left atrial appendage occluder according to claim 1, wherein the proximal disk surface and the distal disk surface forming a structure having a conical surface with a vertex angle.

18. The left atrial appendage occluder according to claim 17, wherein the proximal seal head is inside the structure having the conical surface, and the distal seal head being at the vertex angle of the structure outside the conical surface.

19. The left atrial appendage occluder according to claim 14, wherein the proximal disk surface comprises a proximal seal head, the proximal seal head being inside the structure having the conical surface;
    one end of each proximal supporting rod is connected with the proximal seal head, and the other end of each proximal supporting rod is radiated in the radial direction and is hanging;
    the distal disk surface comprises a distal seal head, the distal seal head being at the vertex angle of the structure outside the conical surface; and
    one end of each distal supporting rod is connected with the distal seal head, and the other end of each distal supporting rod is radiated in the radial direction and is hanging.

* * * * *